United States Patent [19]
Levine et al.

[11] 4,061,108
[45] Dec. 6, 1977

[54] SLIDE SMEARING DEVICE

[75] Inventors: Marshall S. Levine, Wayne; Albert A. Faulkner, Conshohocken, both of Pa.

[73] Assignee: SmithKline Corporation, Philadelphia, Pa.

[21] Appl. No.: 688,101

[22] Filed: May 19, 1976

[51] Int. Cl.² .......................................... B05C 11/04
[52] U.S. Cl. ................................. 118/100; 118/104; 118/120; 427/2
[58] Field of Search ............... 118/104, 108, 100, 120, 118/203, 256; 427/2, 8

[56] References Cited

U.S. PATENT DOCUMENTS

| | | | |
|---|---|---|---|
| 3,175,646 | 3/1965 | Wilcox | 188/94 |
| 3,470,847 | 10/1969 | Chapin et al. | 118/100 |
| 3,683,850 | 8/1972 | Grabhorn | 118/100 |
| 3,880,111 | 4/1975 | Levine et al. | 118/100 X |
| 3,888,206 | 6/1975 | Faulkner | 118/100 |

FOREIGN PATENT DOCUMENTS

| | | | |
|---|---|---|---|
| 439,124 | 1/1927 | Germany | 118/120 |

*Primary Examiner*—Mervin Stein
*Attorney, Agent, or Firm*—Smith, Harding, Earley & Follmer

[57] ABSTRACT

A device for smearing liquid on a slide has (1) a housing and means for supporting a pair of slides on top of the housing, (2) a carriage with a pair of spaced runners which slidably support the carriage on the top of the housing, (3) a spreader pivotally mounted on the carriage and free to rock transversely with respect to a slide, (4) a member to advance the carriage and spreader, (5) a spring and dashpot arrangement to retract the carriage, and (6) latch means to arrest the carriage after it retracts a short distance. The means for supporting the slides may support the slide at an angle of at least five degrees with respect to the plane in which the carriage moves reducing the thickness of the liquid smeared on the slide. The dashpot plunger moves in the direction of an open end of the dashpot cylinder. Advantageously the device has means to clean the spreader.

30 Claims, 16 Drawing Figures

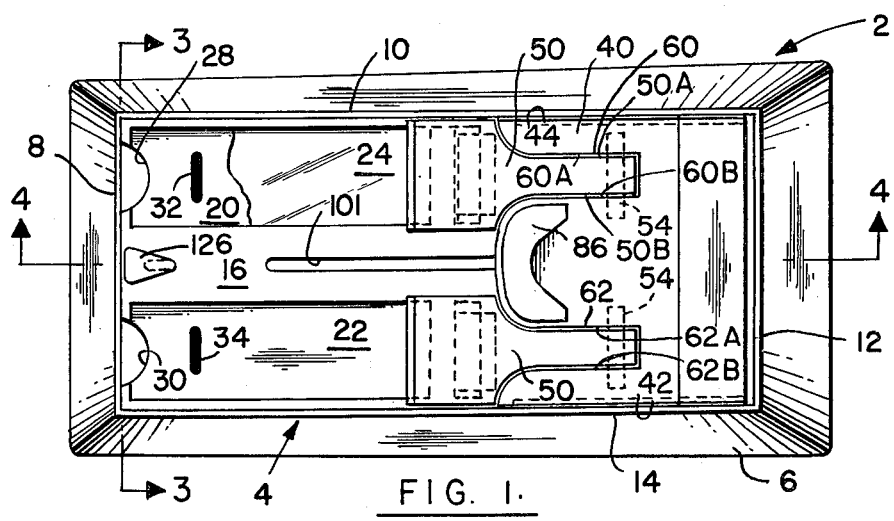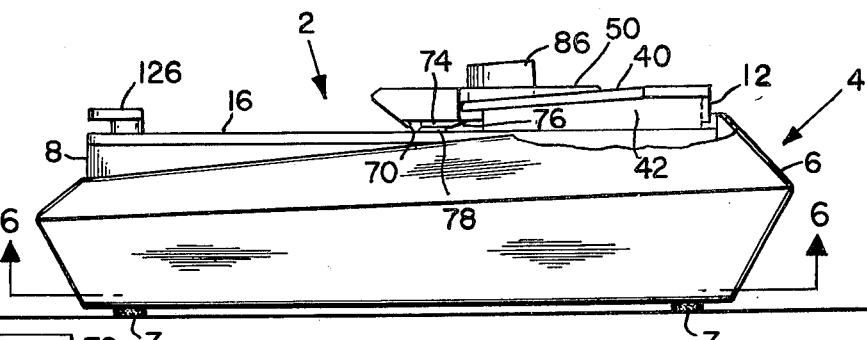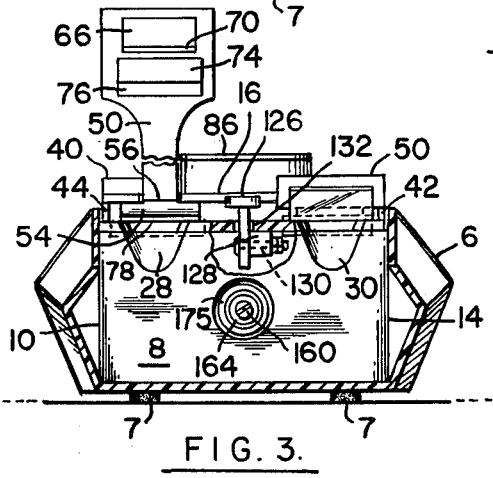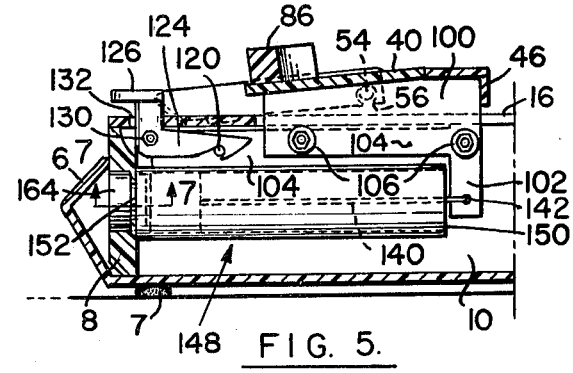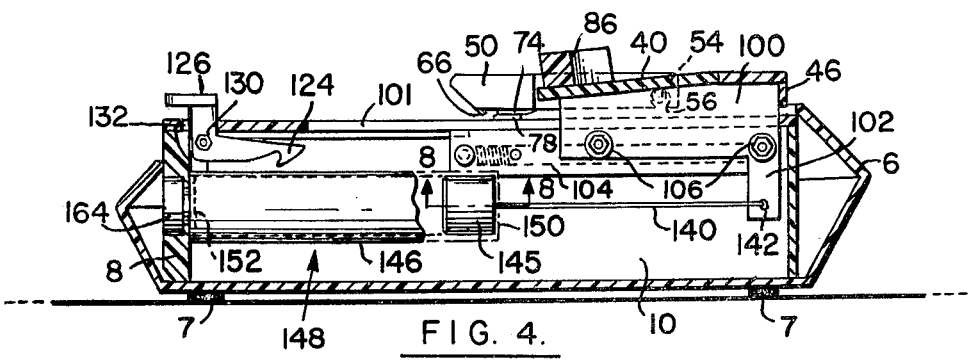

SLIDE SMEARING DEVICE

BACKGROUND OF THE INVENTION

It is well known to smear a liquid on a slide and then subject the liquid to examination under a microscope. This is done widely, for example, with blood to make a white blood cell differential count. The quality of the smear is important. Thus, automatic blood cell differential analyzers cannot provide an accurate white blood cell differential count unless there is an adequate uniform area of blood cell monolayer in the smear. Not only is it important to provide a good smear, but it is also important to provide uniformity of smear from one slide to another.

Prior art devices for smearing a slide are shown in the following patents:

German Pat. No. 439,124—Jan. 24, 1927
U.S. Pat. No. 3,683,850—Aug. 15, 1972
U.S. Pat. No. 3,880,111—Apr. 29, 1975

The device of the German patent is unsatisfactory since it is not possible to control the speed of the spreader while smearing manually to provide either a good smear or smears which are uniform from one smear to the other. While U.S. Pat. Nos. 3,683,850 and 3,880,111 disclose good devices, they lack the highly advantageous features provided by the invention. The prior art fails to teach the mounting of the carriage on a pair of spaced runners which provides for smooth travel of the carriage with low friction and a low rate of wear. The novel spreader which is pivotally mounted and free to rock transversely is advantageous over the prior art since it can accommodate itself to the surface of the slide. While spring and dashpot drive means have been employed as, for example, in U.S. Pat. No. 3,683,850, their use has resulted in considerable vibration being transmitted to the spreader to the detriment of the smear due to the fact that the plunger of the dashpot during the drive portion of the cycle moves from the open end of the dashpot towards the closed end having a restricted opening and hence operates against a column of air causing a flutter or vibration. The invention also provides means to bring the spreader into contact with a liquid deposited on the slide and then move it a short distance away to separate excess liquid from the liquid to be smeared which then moves along the length of the spreader by capillary action. This prevents the spreader from smearing too much liquid on the slide when an excessive amount of liquid is placed on the slide. The prior art also fails to disclose means to support the slide at an angle of at least 5°, preferably in the range of 5° to 8°, to the plane in which the carriage moves in order to cause a decrease in the angle between the spreader and the slide as the smearing action takes place. While slides have been placed at a slight angle to the plane in which the carriage supporting the spreader moves incident to structures which provide for accommodating slides of different lengths, as in U.S. Pat. No. 3,880,111, the resultant angles were too small to effect any significant decrease in the thickness of the smear. A novel combination of means for advancing the spreader and releasing the spreader for retraction provides for the proper time delay for the liquid to spread along the spreader. It is also known in the art to use a loose fitting spreader on a pin along with restricting sleeves on the pin to permit the spreader to move vertically and rock but to be restricted in its side to side movement. This invention eliminates the complexity of the sleeves by employing restricting side walls adjacent the spreader.

BRIEF SUMMARY OF THE INVENTION

A device for smearing on a slide a liquid placed at a predetermined position on the slide has a housing and means for supporting a slide on the top of the housing. A reciprocable carriage is mounted on the top of the housing and carries a spreader adapted to engage the slide. The carriage is movable with respect to the slide in one direction to move the spreader into contact with the liquid on the slide. Drive means retracts the carriage at a predetermined speed in the opposite direction to cause the spreader to smear the liquid on the slide. Advantageously a pair of slide supporting means and spreaders are used. The invention has one or more of the following features. In one feature the drive means comprises a spring and an air dashpot having a cylinder with an open end and a closed end with restrictor means in the closed end and a piston connected to the carriage adjacent the open end when the carriage is retracted. Another feature comprises means to arrest the retraction of the carriage with the spreader a short distance from the predetermined position on the slide where the liquid is placed to provide for the spreader to separate out from the said liquid a predetermined amount of the liquid and to permit the liquid separated out to move along the width of the spreader before the spreader is retracted to its original position to form the smear on the slide. Another feature comprises a spreader pivotally mounted on the carriage and free to rock transversely with respect to the slide to permit the spreader to accommodate itself to the surface of the slide. A further feature comprises a pair of spaced runners on the carriage and slidably supporting the carriage on the top of the housing. Another feature comprises having the means for supporting a slide on the top of the housing support the slide at an angle of at least 5° to the plane in which the carriage moves to place the end of the slide closest to the point where the liquid is placed above the opposite end of the slide to provide for a decrease in the angle between the spreader and the slide as the liquid is being smeared on the slide to assist in reducing the thickness of the smear. A still further feature is that the relationship between the means for advancing the slide and the means to release the slide for retraction is such that the operator automatically provides the desired time delay for the liquid to spread along the spreader. Advantageously a pair of slides and a pair of spreaders are employed. Further means to clean the spreader is provided.

BRIEF DESCRIPTION OF THE DRAWINGS

FIG. 1 is a top plan view of a slide smearing device in accordance with the invention;

FIG. 2 is a right side elevation of the device of FIG. 1;

FIG. 3 is a vertical section taken on the plane indicated by the line 3—3 in FIG. 1 with one of the spreaders shown in an elevated position;

FIG. 4 is a vertical section taken on the plane indicated by the line 4—4 in FIG. 1;

FIG. 5 is a view partially broken away showing a portion of the parts shown in FIG. 4 with the carriage in the latched position;

DETAILED DESCRIPTION

Figure 6:
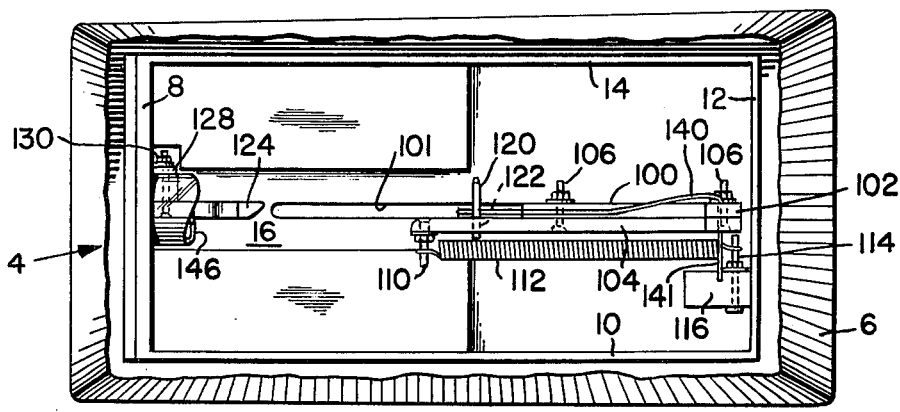
FIG. 6 is a vertical section taken on the plane indicated by the line 6—6 in FIG. 2.

As seen in FIG. 1, a blood smearing device 2 has a housing 4 seated inside an open topped base member 6 mounted on rubber feet 7. Housing 4 has a front wall 8, a left side wall 10, a rear wall 12, a right side wall 14 and a top 16, the bottom being open. Top 16 lies in a horizontal plane and has a pair of recesses 20 and 22 each for the reception of a glass microscope slide 24. Notches 28 and 30 are provided to assist in getting a finger under a slide in recesses 20 and 22, respectively. Transverse lines 32 and 34 are painted on the bottom of recesses 20 and 22, respectively, to indicate to the operator where the liquid should be placed on the glass slides 24.

A carriage 40 has downwardly extending elongated runners 42 and 44 which rest on the top 16. Runners 42 and 44 are relatively narrow to provide for a minimum of friction and are placed on opposite sides of carriage 40 to provide a maximum of stability. The use of these runners provides for a minimum of wear, keeps the number of parts to a minimum and provides for smooth and low friction movement of the carriage. At their rear ends, slide members 42 and 44 are connected by a wall 46 (FIG. 5) the lower end of which lies above top 16.

Figure 11:
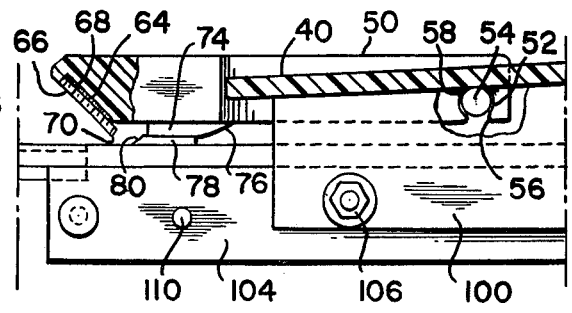
FIG. 11 is an enlarged vertical sectional view, partially broken away, showing a spreader of the device of FIG. 1 at rest.

A pair of spreaders 50, 50 each have a recess 52 into which a pin 54 is snapped through a reduced neck portion 56 (see FIG. 11). Each pin 54 is secured by an adhesive indicated at 58 (FIG. 11) to the underside of carriage 40. One spreader 50 having parallel walls 50A and 50B is accommodated in an opening 60 (FIG. 1) through carriage 40 which is bounded by opposed walls 60A and 60B and the other spreader 50 is accommodated in an opening 62 through carriage 40 which is bounded by walls 62A and 62B, in each case the opening being relatively long compared to its width and providing a loose fit for the spreader. Each pin 54 also fits loosely within its corresponding opening 52 (FIG. 11). Thus each spreader 50 can freely pivot vertically and also can rock transversely which permits the spreader to accommodate itself to the surface of the slide 24 with which it is associated. Walls 60A and 60B restrict one spreader 50 from side to side movement in a generally horizontal plane while walls 62A and 62B do the same for the other spreader 50. Each spreader 50 has a front recess 64 (FIG. 11) in which a rectangular panel of glass 66 is secured by double adhesive tape 68. The lower edge 70 of panel 66 is adapted to engage a glass slide 24. Each spreader 50 has a cam 74 with a rearwardly facing sloping face 76 which coacts with a cam 78 with a frontwardly facing sloping face 80 and secured to the top 16 of housing 4.

An upstanding finger hold member 86 (FIG. 1) is secured to carriage 40, the operator advancing carriage 40 by placing his index finger in member 86 and his thumb against the front 8 of housing 4 and squeezing the index finger and thumb together.

Carriage 40 has a centrally located depending bar 100 (FIG. 4) which extends downwardly through slot 101 in the top 16 of housing 4. Bar 100 has a depending leg 102 at its rear end and is secured to a bar 104 (FIG. 4), which rides up against the lower face of top 16, by bolts indicated at 106, 106. Bar 104 has a pin 110 (FIG. 6) secured at its forward end which is connected to one end of an extension coil spring 112 which has its other end connected to a pin 114 secured to a block 116 which, in turn, is secured to housing 4. A pin 120 secured by a pressed fit in opening 122 in bar 104 is adapted to be engaged by a latch 124 which has an upstanding operating member 126. A block 128 secured to housing 4 carries a pivot member 130 on which lever 124 is pivoted. Member 126 passes through an opening 132 in top 16.

Slot 101 permits bar 100 to be advanced towards the front of the smearing device 2 until the edge 70 of each glass panel 66 is approximately centered over the liquid deposited on the slides 24. At this juncture pin 120 is typically about one-eighth of an inch forward of its latch engaged position.

A rod 140 (FIG. 4) has its rear end 141 secured to leg 102 through an opening 142 in the leg and has its forward end fixedly secured to a ball valve 144 (FIG. 8) within a plunger 145 mounted in a cylinder 146 of a dashpot 148 (FIG. 4). Cylinder 146 has an open end 150 and a closed end 152 which has a small conical opening 154 (FIG. 7) controlled by the conical end 156 of a threaded plug 158 which has a slot 160 for the reception of a screwdriver. Plug 158 is threadably connected to the head 164 of the closed end of cylinder 146 which is secured in an opening 168 in wall 8 by a nut 170 threadably secured to threads 166 on head 164.

Ball valve 144 controls an opening 180 in cap 182 (FIG. 8) being urged to close the opening by a loosely coiled flat spiral spring 184 which abuts against the ball valve 144 and against a hollow boss 186 of plate 188. Cap 182 is secured by a pressed fit to boss 186. Plate 188 is secured by a pressed fit in a recessed portion 190 of a sleeve 192 which is secured by a pressed fit inside the open end of cylinder 146. Plate 188 has a central opening 202 receiving a hollow pin 204 which has a pair of slots 206, 206 in its end adjacent spring 184. Air can pass through pin 204, slots 206, through spring 184 and around ball valve 144 to pass through opening 180 when it is not closed by ball valve 144. The end of pin 204 adjacent spring 184 limits the travel of the spring 184 and ball valve 144 in the forward direction away from opening 180. The thus described dashpot is known to the art being of the type disclosed in United States Patent 3,175,646, the disclosure of which is incorporated herein by reference.

OPERATION

Figure 7:
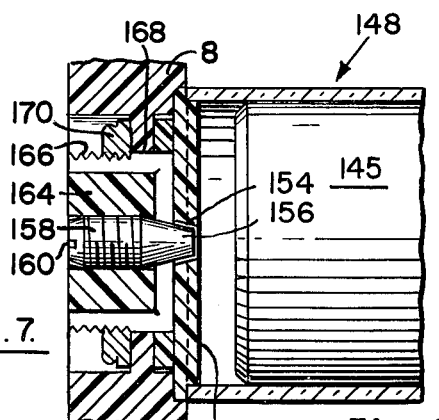
FIG. 7 is an enlarged sectional view taken on the line 7—7 in FIG. 5 through the air metering device in the dashpot of the device of FIG. 1.
Figure 8:
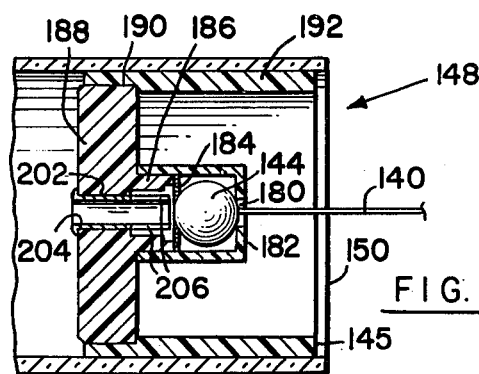
FIG. 8 is an enlarged sectional view taken on line 8—8 in FIG. 4 and partially broken away showing the dashpot plunger of the device of FIG. 1.
Figure 9:
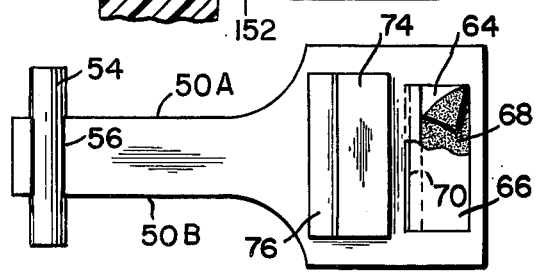
FIG. 9 is an enlarged bottom plan view of a spreader of the device of FIG. 1 and its associated supporting pin.
Figure 10:
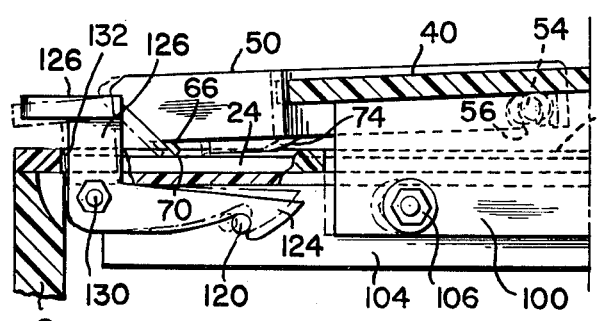
FIG. 10 is an enlarged vertical sectional view, partially broken away, of the device of FIG. 1 showing the carriage latch arrangement.

In order to operate the slide smearing device 2, a glass slide 24 is inserted in each of recesses 20 and 22. A drop of the liquid to be smeared is placed on the slide where indicated by the lines 32 and 34, the use of a line as against a spot encouraging the spread of the drop across the slides. The operator's index finger now engages member 86 on carriage 40 and his adjacent thumb engages front wall 8 and they are squeezed together in order to advance carriage 40 towards the front of device 2. As carriage 40 is advanced rod 140 urges ball valve 144 against spring 184 to clear opening 180 for the passage of air to facilitate the advance of plunger 145. Spreader cams 74 slide off cams 78 permitting spreaders 40 to lower to place the edges 70 of glass panels 66 against the respective slides 24. Carriage 40 is advanced until the forward edge of bar 100 contacts the forward end of slot 101 to arrest the movement of carriage 40 with the edges 70 of panels 66 substantially centered in the liquid deposited on the slides. The operator now releases the carriage 40 which is retracted by extension coil spring 112 which has been extended by the advance of the carriage. Latch 124 engages pin 120, the latch 124 being urged downwardly by gravity. This stops the movement of carriage 140 after it has traveled a short distance. For maximum smoothness in the operation of dashpot 148 during the smearing, the plunger 145 should not be more than ⅛ inch from the closed end 152 of cylinder 146 when the carriage is held in the latched position. This initial action provides for the glass panels to separate out from the deposited liquid the desired amount of liquid to be smeared which then spreads along the width of each glass panel. This initial separation of liquid from the originally deposited liquid insures that an excessive amount of liquid will not be carried by the spreader and avoids having a smear of excessive thickness particularly where an excess amount of liquid has been deposited on a slide. As soon as the operator releases carriage 40 he moves his index finger to lever 126 which he rocks counterclockwise as viewed in FIG. 10 to move latch 124 upwardly and release pin 120. The time to carry out this movement provides a proper amount of time for the liquid to spread along the glass panels before the smearing operation. As soon as latch 124 releases pin 120 spring 112 retracts carriage 40, the speed of retraction being controlled by the dashpot 148. As best seen in FIG. 7 this speed can be controlled by varying the position of conical plug 156 and opening 154 to control the rate at which air can enter cylinder 146. During this operation, bar 140 is pulling ball valve 144 into tight engagement with opening 180 so that no air can pass through this opening. As the glass panels 66 are retracted over slides 24, they smear the liquid on the slides in a decreasing thickness. The edges 70 of the panels 66 can freely accommodate themselves to the slides by virtue of being mounted on pins 54 for vertical movement and being mounted on these pins and within slots 60 and 62, respectively, so that they can rock transversely. A very smooth action of the dashpot 148 is achieved by virtue of the plunger 145 in effect pulling air into cylinder 146 and advancing against air which can freely pass through opening 150 which eliminates the flutter or vibration caused when the plunger operates in the reverse direction against a column of air to provide dampening as is done in the prior art. The cams 74 of spreaders 50 are retracted against their respective cams 78 which causes the spreaders to be elevated above slides 24 before they come to rest to permit the free removal of the slides. The spaced runners 42 and 44 travel smoothly on top 16 providing for smooth travel of the carriage and thus preventing distortion of the liquid smears.

Figure 12:
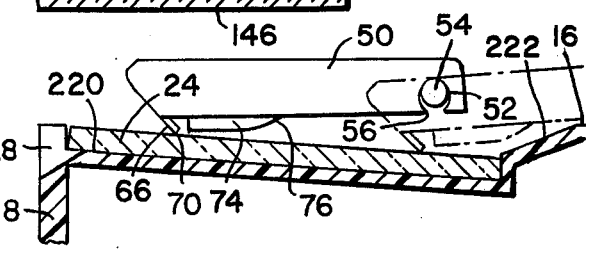
FIG. 12 is a vertical sectional view showing a modified angled slide supporting means.

As shown in FIG. 12, an alternative angled recess 220 may be placed in top 16 to receive a slide 24 and dispose it at an angle of, for example, 5° to provide for a greater decrease in thickness of the smear of the liquid. This results from the decrease in the angle between the glass panel 66 and the slide 24 as the spreader 50 lowers during retraction. In this modification the top 16 has been chamfered at 222 to engage cam 74 and cam spreader 50 up off slide 24 at the end of its retraction.

The operation of the embodiment of FIG. 12 is essentially the same as described above with the exception that as the spreader 50 is retracted it lowers, changing the angle between glass plates 66 and slide 24 causing an additional decrease in the thickness of the liquid smeared. Also, cam 74 on spreader 50 engages a chamfered portion 222 of top 16 causing spreader 50 to be elevated above slide 24 at the end of its travel.

Figure 13:
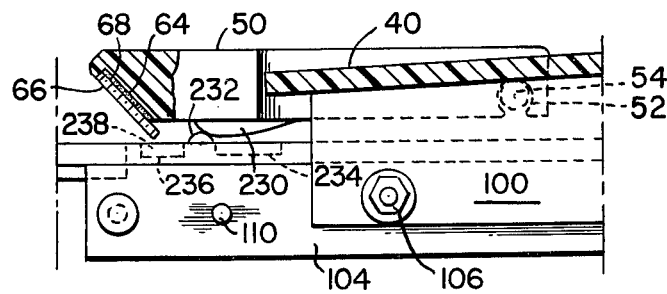
FIG. 13 is an enlarged vertical sectional view, partially broken away, showing means for cleaning the spreader.
Figure 14:
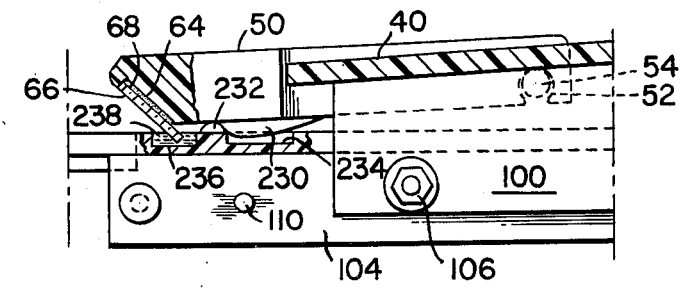
FIG. 14 is a sectional view of the structure of FIG. 13 in the spreader cleaning position.

As shown in FIGS. 13 and 14, the device of FIG. 1 may be modified to provide for cleaning of the glass panel 66 of a spreader 50. Cams 230 and 232 are substituted for cams 74 and 78, respectively. A recess 234 in housing top 16 is adapted to receive cam 230. A reservoir 236 contains a cleaning liquid 238. The liquid selected will be one suitable for cleaning the liquid being spread off spreader panel 66, for example, water where the liquid spread is blood. Cams 230 and 232 perform the functions of lowering the spreader panel 66 onto a slide as the spreader 50 is advanced and lifting it off the slide when the spreader is retracted as in the case of the device of FIG. 1. Additionally they lower spreader panel into liquid 238 as the spreader 50 is fully retracted and as cam 230 drops down on the rear face of cam 232 and enters recess 234. Liquid 238 acts to clean the spread liquid off spreader panel 66. When the spreader 50 is advanced, the cams 230 and 232 act to lift spreader panel 66 clear of liquid 238 and reservoir 236.

Figure 15:
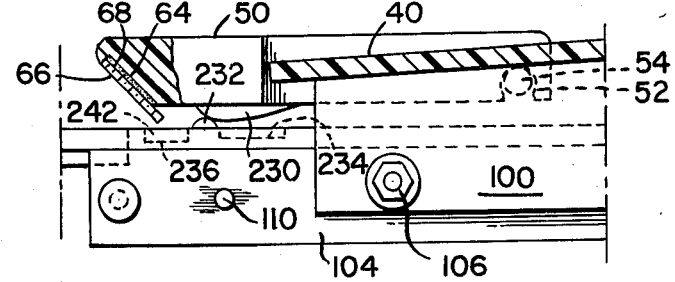
FIG. 15 is an enlarged vertical sectional view, partially broken away, showing alternative means for cleaning the spreader.
Figure 16:
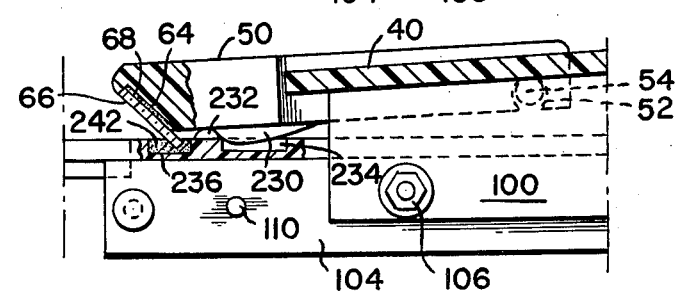
FIG. 16 is a sectional view of the structure of FIG. 15 in the spreader cleaning position.

As shown in FIGS. 15 and 16, a cleansing medium other than water can be employed, for example, an absorbent material such as felt 242 can be placed in reservoir 236. If desired, the felt can be saturated with a cleaning liquid such as water. Paper and fabrics are further exemplary of satisfactory cleaning media.

The above described embodiments are illustrative and are not intended to be limiting.

We claim:

1. A device for smearing on a slide a liquid placed at a predetermined position on the slide comprising:
   a housing,
   means for supporting a slide on the top of the housing,
   a reciprocable carriage mounted on the top of the housing,
   a spreader mounted on the carriage and adapted to engage the slide,
   said carriage being movable with respect to the slide in one direction to move the spreader to said predetermined position on the slide and into contact with the liquid,
   drive means to retract the carriage at a predetermined speed in the opposite direction to cause the spreader to smear the liquid on the slide,
   said drive means including a spring and an air dashpot having a cylinder with means to restrict the passage of air through one end and being open at its other end and a piston connected to the carriage adjacent the open end when the carriage is retracted, and the restricting means being adjustable to provide for the selection of different retracting speeds.

2. A device in accordance with claim 1 having means to arrest the initial retraction of the carriage with the spreader a short distance from said predetermined position to permit the liquid adjacent the spreader to move along the width of the spreader before the spreader is retracted to its original position, and means to release the carriage from said arrested position.

3. A device in accordance with claim 1 in which the spreader has side walls of substantial length and is loosely mounted on a pin secured to the carriage for pivoting vertically and rocking transversely with respect to a slide and the carriage has a pair of opposed walls spaced from said side walls to accommodate the rocking of the spreader and restrict the side to side movement of the spreader.

4. A device in accordance with claim 1 having a pair of spaced runners on the carriage and in which the housing has a substantially flat and horizontal surface to support each runner for sliding movement.

5. A device in accordance with claim 1 in which the means for supporting a slide supports the slide at an angle of at least 5° to the plane in which the carriage reciprocates to place the end of the slide closest to said predetermined position above the opposite end of the slide to cause the angle between the spreader where it engages the slide and the slide to decrease as the liquid is being smeared on the slide to reduce the thickness of the smear.

6. A device in accordance with claim 1 having means to clean the spreader as it reaches its retracted position.

7. A device for smearing on a slide a liquid placed at a predetermined position on the slide comprising:
a housing,
means for supporting a slide on the top of the housing,
a reciprocable carriage mounted on the top of the housing,
a spreader mounted on the carriage and adapted to engage the slide,
said carriage being movable with respect to the slide in one direction to move the spreader to said predetermined position on the slide and into contact with the liquid,
drive means to retract the carriage at a predetermined speed in the opposite direction to cause the spreader to smear the liquid on the slide, and
means to arrest the initial retraction of the carriage with the spreader a short distance from said predetermined position to permit the liquid adjacent the spreader to move along the width of the spreader before the spreader is retracted to its original position, and means to release the carriage from said arrested position.

8. A device in accordance with claim 7 in which the spreader has side walls of substantial length and is loosely mounted on a pin secured to the carriage for pivoting vertically and rocking transversely with respect to a slide and the carriage has a pair of opposed walls spaced from said side walls to accommodate the rocking of the spreader and restrict the side to side movement of the spreader.

9. A device in accordance with claim 7 having a pair of spaced runners on the carriage and in which the housing has a substantially flat and horizontal surface to support each runner for sliding movement.

10. A device in accordance with claim 7 in which the means for supporting a slide supports the slide at an angle of at least 5° to the plane in which the carriage reciprocates to place the end of the slide closest to said predetermined position above the opposite end of the slide to progressively reduce the angle where the spreader meets the slide as the smear is being made to reduce the thickness of the smear.

11. A device in accordance with claim 7 having means to clean the spreader as it reaches its retracted position.

12. A device for smearing on a slide a liquid placed at a predetermined position on the slide comprising:
a housing,
means for supporting a slide on the top of the housing,
a reciprocable carriage mounted on the top of the housing,
a pin secured to the carriage,
a spreader having side walls of substantial length loosely mounted on the pin for pivoting vertically and rocking transversely with respect to a slide,
a pair of opposed walls on the carriage spaced from the side walls of the spreader accommodating the rocking of the spreader and restricting the side to side movement of the spreader,
said carriage being movable with respect to the slide in one direction to move the spreader to said predetermined position on the slide and into contact with the liquid, and
drive means to retract the carriage at a predetermined speed in the opposite direction to cause the spreader to smear the liquid on the slide.

13. A device in accordance with claim 12 having means to arrest the initial retraction of the carriage with the spreader a short distance from said predetermined position to permit the liquid adjacent the spreader to move along the width of the spreader before the spreader is retracted to its original position, and means to release the carriage from said arrested position.

14. A device in accordance with claim 12 having a pair of spaced runners on the carriage and in which the housing has a substantially flat and horizontal surface to support each runner for sliding movement.

15. A device in accordance with claim 12 in which the means for supporting a slide supports the slide at an angle of at least 5° to the plane in which the carriage reciprocates to place the end of the slide closest to said predetermined position above the opposite end of the slide to cause the angle between the spreader where it engages the slide and the slide to decrease as the liquid is being smeared on the slide to reduce the thickness of the smear.

16. A device in accordance with claim 12 having means to clean the spreader as it reaches its retracted position.

17. A device for smearing on a slide a liquid placed at a predetermined position on the slide comprising:
a housing,
means for supporting a slide on the top of the housing,
a reciprocable carriage,
spaced runners on the carriage, the housing having a substantially flat and horizontal surface to support each runner for sliding movement, a spreader mounted on the carriage and adapted to engage the slide, said carriage being movable with respect to the slide in one direction to move the spreader to said predetermined position on the slide and into contact with the liquid, and drive means to retract the carriage at a predetermined speed in the opposite direction to cause the spreader to smear the liquid on the slide.

18. A device in accordance with claim 17 having means to arrest the initial retraction of the carriage with the spreader a short distance from said predetermined position to permit the liquid adjacent the spreader to move along the width of the spreader before the spreader is retracted to its original position, and means to release the carriage from said arrested position.

19. A device in accordance with claim 17 in which the spreader has side walls of substantial length and is loosely mounted on a pin secured to the carriage for pivoting vertically and rocking transversely with respect to a slide and the carriage has a pair of opposed walls spaced from said side walls to accommodate the rocking of the spreader and restrict the side to side movement of the spreader.

20. A device in accordance with claim 17 in which the means for supporting a slide supports the slide at an angle of at least 5° to the plane in which the carriage reciprocates to place the end of the slide closest to said predetermined position above the opposite end of the slide to cause the angle between the spreader where it engages the slide and the slide to decrease as the liquid is being smeared on the slide to reduce the thickness of the smear.

21. A device in accordance with claim 17 having means to clean the spreader as it reaches its retracted position.

22. A device for smearing on a slide a liquid placed at a predetermined position on the slide comprising:

a housing, means for supporting a slide on the top of the housing, a reciprocable carriage mounted on the top of the housing, a spreader mounted on the carriage and adapted to engage the slide, said carriage being movable with respect to the slide in one direction to move the spreader to said predetermined position on the slide and into contact with the liquid, and drive means to retract the carriage at a predetermined speed in the opposite direction to cause the spreader to smear the liquid on the slide, said slide supporting means supporting a slide at an angle of at least 5° to the plane in which the carriage reciprocates to place the end of the slide closest to said predetermined position above the opposite end of the slide to cause the angle between the spreader where it engages the slide and the slide to decrease as the liquid is being smeared on the slide to reduce the thickness of the smear.

23. A device in accordance with claim 22 having means to arrest and initial retraction of the carriage with the spreader a short distance from said predetermined position to permit the liquid adjacent the spreader to move along the width of the spareder before the spreader is retracted to its original position, and means to release the carriage from said arrested position.

24. A device in accordance with claim 22 in which the spreader has walls of substantial length and is loosely mounted on a pin secured to the carriage for pivoting vertically and rocking transversely with respect to a slide and the carriage has a pair of opposed walls spaced from said side walls to accommodate the rocking of the spreader and restrict the side to side movement of the spreader.

25. A device in accordance with claim 22 having a pair of spaced runners on the carriage and slidably supporting the carriage on the housing.

26. A device in accordance with claim 22 having means to clean the spreader as it reaches its retracted position.

27. A device for smearing on a slide a liquid placed at a predetermined position on the slide comprising:

a housing, means for supporting a slide on the top of the housing, a reciprocable carriage mounted on the top of the housing, a spreader mounted on the carriage and adapted to engage the slide, said carriage being movable with respect to the slide in one direction to move the spreader to said predetermined position on the slide and into contact with the liquid, drive means to retract the carriage at a predetermined speed in the opposite direction to cause the spreader to smear the liquid on the slide, and means to clean the spreader after it has smeared the liquid, 28. A device in accordance with claim 27 in which the cleaning means includes a liquid reservoir.

29. A device in accordance with claim 27 in which the cleaning means includes an absorbent material.

30. A device in accordance with claim 27 having means to lower the spreader into the cleaning means as it is retracted and to elevate the spreader above the cleaning means as it is advanced.

* * * * *

UNITED STATES PATENT AND TRADEMARK OFFICE
CERTIFICATE OF CORRECTION

PATENT NO. : 4,061,108
DATED : December 6, 1977
INVENTOR(S) : Marshall S. Levine and Albert A. Faulkner It is certified that error appears in the above-identified patent and that said Letters Patent are hereby corrected as shown below:

In column 10, line 10, (claim 23), "and" should read "the"; line 13, (claim 23), "spareder" should read "spreader"; line 18, (claim 24), insert - - side - - before "walls"; line 48, (claim 27), "," should be ".".

Signed and Sealed this

Seventh Day of March 1978

[SEAL]

Attest:

RUTH C. MASON
*Attesting Officer*

LUTRELLE F. PARKER
*Acting Commissioner of Patents and Trademarks*